United States Patent
Nguyen et al.

(10) Patent No.: US 11,678,989 B2
(45) Date of Patent: Jun. 20, 2023

(54) BIODEGRADABLE PIEZOELECTRIC NANOFIBER SCAFFOLD FOR BONE OR TISSUE REGENERATION

(71) Applicant: University of Connecticut, Farmington, CT (US)

(72) Inventors: Thanh Duc Nguyen, South Windsor, CT (US); Ritopa Das, Farmington, CT (US)

(73) Assignee: UNIVERSITY OF CONNECTICUT, Farmington, CT (US)

( * ) Notice: Subject to any disclaimer, the term of this patent is extended or adjusted under 35 U.S.C. 154(b) by 355 days.

(21) Appl. No.: 16/806,902

(22) Filed: Mar. 2, 2020

(65) Prior Publication Data

US 2020/0276018 A1    Sep. 3, 2020

Related U.S. Application Data

(60) Provisional application No. 62/812,499, filed on Mar. 1, 2019.

(51) Int. Cl.
*A61F 2/28* (2006.01)
*A61L 27/58* (2006.01)
(Continued)

(52) U.S. Cl.
CPC .............. *A61F 2/28* (2013.01); *A61L 27/18* (2013.01); *A61L 27/34* (2013.01);
(Continued)

(58) Field of Classification Search
CPC ............... A61F 2/28; A61F 2002/2821; A61F 2002/2864; A61F 2002/30062;
(Continued)

(56) References Cited

U.S. PATENT DOCUMENTS

| 589,119 A | 8/1897 | Burgess |
| 5,131,276 A * | 7/1992 | Kibblewhite ......... B06B 1/0662 73/761 |

(Continued)

FOREIGN PATENT DOCUMENTS

| WO | WO2006057987 A1 | 6/2006 |
| WO | WO2008085904 A1 | 7/2008 |

(Continued)

OTHER PUBLICATIONS

Amini et al., "Bone tissue engineering: recent advances and challenges," Critical Reviews™ in Biomedical Engineering, 2012, 40,(5):363-408.

(Continued)

*Primary Examiner* — Jennifer Dieterle
*Assistant Examiner* — Melissa A Hoban
(74) *Attorney, Agent, or Firm* — Myers Wolin, LLC

(57) ABSTRACT

A scaffold comprised of a plurality of PLLA layers, which may include stem cells, for regenerating bone or tissue. The PLLA layers are separated by a plurality of hydrogel layers. The PLLA layers comprise a nanofiber mesh having a piezoelectric constant to apply an electrical charge to the bone or tissue upon application of ultrasound energy.

19 Claims, 8 Drawing Sheets
(8 of 8 Drawing Sheet(s) Filed in Color)

(51) Int. Cl.
  *A61L 27/34* (2006.01)
  *A61L 27/18* (2006.01)
  *A61L 27/54* (2006.01)
  *A61L 27/38* (2006.01)
  *A61F 2/30* (2006.01)

(52) U.S. Cl.
  CPC .......... *A61L 27/3847* (2013.01); *A61L 27/54* (2013.01); *A61L 27/58* (2013.01); *A61F 2002/2821* (2013.01); *A61F 2002/2864* (2013.01); *A61F 2002/30062* (2013.01); *A61F 2002/3084* (2013.01); *A61F 2002/30087* (2013.01); *A61F 2002/30677* (2013.01); *A61F 2002/30971* (2013.01); *A61L 2400/12* (2013.01); *A61L 2430/02* (2013.01)

(58) Field of Classification Search
  CPC .. A61F 2002/30087; A61F 2002/30677; A61F 2002/3084; A61F 2002/30971; A61F 2/3094; A61F 2310/00293; A61F 2310/00371; A61F 2/2846; A61F 2310/00982; A61L 27/18; A61L 27/34; A61L 27/3847; A61L 27/54; A61L 27/58; A61L 2400/12; A61L 2430/02; A61L 27/3834; A61L 27/46; A61L 27/24; A61L 27/52; A61L 27/56
  See application file for complete search history.

(56) References Cited

U.S. PATENT DOCUMENTS

| | | | | |
|---|---|---|---|---|
| 5,246,013 | A * | 9/1993 | Frank | A61B 5/0053 600/587 |
| 5,287,331 | A * | 2/1994 | Schindel | H04R 17/005 29/25.35 |
| 5,443,495 | A * | 8/1995 | Buscemi | A61F 2/82 623/1.21 |
| 5,512,600 | A * | 4/1996 | Mikos | D04H 1/4266 521/76 |
| 5,514,378 | A * | 5/1996 | Mikos | A61F 2/4241 521/27 |
| 5,678,565 | A * | 10/1997 | Sarvazyan | G01S 7/52042 600/587 |
| 5,794,023 | A * | 8/1998 | Hobbs | G02B 26/0808 359/576 |
| 5,827,198 | A * | 10/1998 | Kassal | B06B 1/0688 310/368 |
| 6,142,948 | A * | 11/2000 | Toda | A61B 5/02007 600/459 |
| 6,447,887 | B1 * | 9/2002 | Claus | H01L 41/193 428/209 |
| 6,468,219 | B1 * | 10/2002 | Njemanze | A61B 8/065 607/23 |
| 6,627,421 | B1 * | 9/2003 | Unger | C12M 35/04 204/600 |
| 7,396,537 | B1 * | 7/2008 | Krupnick | A61K 47/34 424/443 |
| 8,162,901 | B2 | 4/2012 | Gonnelli et al. | |
| 8,301,262 | B2 | 10/2012 | Mi et al. | |
| 8,708,966 | B2 | 4/2014 | Allen et al. | |
| 8,946,974 | B2 * | 2/2015 | Yu | H01L 41/082 252/62.9 PZ |
| 9,050,053 | B2 * | 6/2015 | Morgan | A61B 8/4281 |
| 9,192,655 | B2 * | 11/2015 | Arinzeh | A61L 27/52 |
| 9,381,680 | B2 | 7/2016 | Oh et al. | |
| 9,527,257 | B2 * | 12/2016 | Lipton | B29C 48/05 |
| 9,846,091 | B2 | 12/2017 | Lu et al. | |
| 10,292,831 | B2 * | 5/2019 | Zellmer | A61B 5/4566 |
| 10,617,880 | B2 * | 4/2020 | Zellmer | A61N 1/326 |
| 10,632,653 | B2 | 4/2020 | Niitsu et al. | |
| 2002/0081732 | A1 * | 6/2002 | Bowlin | A61P 19/08 536/123 |
| 2004/0015211 | A1 * | 1/2004 | Nurmikko | A61B 5/24 607/61 |
| 2004/0018226 | A1 * | 1/2004 | Wnek | B29C 41/006 424/443 |
| 2004/0028655 | A1 * | 2/2004 | Nelson | A61P 5/00 514/18.9 |
| 2005/0248547 | A1 * | 11/2005 | Kent | G06F 3/0436 345/177 |
| 2006/0043843 | A1 * | 3/2006 | Sugiura | G01S 7/521 310/348 |
| 2006/0050189 | A1 * | 3/2006 | Ito | H02N 11/006 349/33 |
| 2006/0107749 | A1 * | 5/2006 | Liu | A61B 5/0002 73/754 |
| 2006/0190080 | A1 * | 8/2006 | Danoff | A61F 2/30721 623/17.11 |
| 2006/0224237 | A1 * | 10/2006 | Furst | A61L 31/16 623/1.42 |
| 2007/0141106 | A1 * | 6/2007 | Bonutti | B05D 1/02 604/20 |
| 2007/0225631 | A1 * | 9/2007 | Bowlin | A61K 38/39 530/356 |
| 2007/0255422 | A1 * | 11/2007 | Wei | A61F 2/30965 264/238 |
| 2007/0293912 | A1 * | 12/2007 | Cowan | A61N 1/326 607/51 |
| 2008/0058633 | A1 * | 3/2008 | Boyden | B33Y 50/00 600/407 |
| 2008/0269666 | A1 | 10/2008 | Wang et al. | |
| 2009/0163965 | A1 * | 6/2009 | Boyden | A61L 2/14 607/3 |
| 2009/0182306 | A1 | 7/2009 | Lee et al. | |
| 2009/0192431 | A1 * | 7/2009 | Horstmann | A61M 37/0092 601/2 |
| 2009/0280153 | A1 * | 11/2009 | Hunter | A61L 27/54 607/2 |
| 2010/0152644 | A1 * | 6/2010 | Pesach | A61M 5/14244 604/20 |
| 2011/0028905 | A1 | 2/2011 | Takada | |
| 2011/0109204 | A1 * | 5/2011 | Tajitsu | H04R 17/005 310/363 |
| 2011/0230747 | A1 | 9/2011 | Rogers et al. | |
| 2011/0242310 | A1 * | 10/2011 | Beebe, Jr. | D01D 5/0069 264/484 |
| 2012/0197155 | A1 | 8/2012 | Mattes et al. | |
| 2012/0226295 | A1 * | 9/2012 | Jabbari | B82Y 30/00 606/151 |
| 2013/0005708 | A1 | 1/2013 | Lalwani | |
| 2013/0041244 | A1 | 2/2013 | Woias et al. | |
| 2013/0140649 | A1 | 6/2013 | Rogers et al. | |
| 2014/0005606 | A1 | 1/2014 | Chen et al. | |
| 2014/0145365 | A1 * | 5/2014 | Omenetto | H01L 41/45 264/479 |
| 2015/0073551 | A1 * | 3/2015 | Uehlin | A61L 27/3834 623/13.12 |
| 2015/0134061 | A1 * | 5/2015 | Friis | A61L 27/446 264/439 |
| 2015/0165020 | A1 | 6/2015 | Jaklenec et al. | |
| 2016/0005951 | A1 | 1/2016 | Yoshida et al. | |
| 2016/0050750 | A1 | 2/2016 | Rogers et al. | |
| 2016/0067375 | A1 * | 3/2016 | Holmes | D01F 1/10 264/129 |
| 2016/0095599 | A1 * | 4/2016 | Jose | A61B 17/11 606/154 |
| 2016/0184571 | A1 | 6/2016 | Admati | |
| 2016/0184595 | A1 | 6/2016 | Hossainy | |
| 2016/0190427 | A1 * | 6/2016 | Kim | H01L 41/193 252/62.9 R |
| 2016/0287668 | A1 | 10/2016 | Tankovich | |
| 2017/0020402 | A1 | 1/2017 | Rogers et al. | |
| 2017/0027168 | A1 * | 2/2017 | Heath | A61P 17/00 |
| 2017/0080196 | A1 | 3/2017 | Lee et al. | |
| 2017/0179370 | A1 | 6/2017 | Kim et al. | |
| 2017/0189660 | A1 | 7/2017 | Baek | |
| 2017/0252546 | A1 | 9/2017 | Park et al. | |
| 2017/0258738 | A1 | 9/2017 | DeMuth et al. | |
| 2017/0268942 | A1 | 9/2017 | Pedder et al. | |

(56) References Cited

U.S. PATENT DOCUMENTS

| | | | |
|---|---|---|---|
| 2017/0368321 | A1 | 12/2017 | Baek |
| 2018/0055643 | A1* | 3/2018 | Castro ................. B33Y 80/00 |
| 2019/0307697 | A1* | 10/2019 | Ma ....................... A61K 9/0024 |
| 2019/0319181 | A1* | 10/2019 | Melands ................ B32B 27/06 |
| 2019/0328285 | A1 | 10/2019 | Liu |
| 2020/0009767 | A1 | 1/2020 | Li |
| 2020/0093966 | A1* | 3/2020 | Rabolt ............... A61B 5/14532 |
| 2020/0276365 | A1* | 9/2020 | Nguyen ................ H01L 41/318 |
| 2020/0313066 | A1* | 10/2020 | Getman ............... A47C 23/002 |

FOREIGN PATENT DOCUMENTS

| | | |
|---|---|---|
| WO | 2017003238 A1 | 1/2017 |
| WO | WO2017011320 A1 | 1/2017 |
| WO | 2019143293 A1 | 7/2019 |

OTHER PUBLICATIONS

Anglen, "The clinical use of bone stimulators," Journal of the Southern Orthopaedic Association, 2002, 12, (2), 46-54.

Bauer et al., "Bone Graft Materials: An Overview of the Basic Science," Clinical orthopaedics and related research, 2000, 371, 10-27.

Bussemer et al., "Pulsatile drug-delivery systems," Crit Rev Ther Drug Syst., 2001, 18(5):433-458, Abstract.

Carpentier et al., "Clinical trial of blood-brain barrier disruption by pulsed ultrasound," Science translational medicine, 2016, 8(343):343re2, 9 pages.

Chen et al., "Fully embeddable chitosan microneedles as a sustained release depot for intradermal vaccination," Biomaterials, 2013, 34(12):3077-3086.

Chiappini et al., "Biodegradable silicon nanoneedles delivering nucleic acids intracellularly induce localized in vivo neovascularization," Nature Materials, 2015, 14:532-539.

Cohen et al., "Totally implanted direct current stimulator as treatment for a nonunion in the foot," The Journal of foot and ankle surgery: official publication of the American College of Foot and Ankle Surgeons, 1993, 32, (4), 375-381.

Csafeglobal, The Cost of a Broken Vaccine Cold Chain Part Two, Financial Cost. <http://csafeglobal.com/the-cost-of-a-broken-vaccine-cold-chain-part-two-financial-cost-1> Sep. 17, 2014, 3 pages.

Curry et al., "Biodegradable piezoelectric force sensor," PNAS, 2018, 115(5):909-914.

Dai et al., "Electrospun emodin polyvinylpyrrolidone blended nanofibrous membrane: a novel medicated biomaterial for drug delivery and accelerated wound healing," Journal of Materials Science: Materials in Medicine, 2012, 23(11):2709-2716.

Demiray, "Electro-mechanical remodelling of bones," International Journal of Engineering Science, 1983, 21, (9), 1117-1126.

Ferreira et al., "Bone Collagen Role in Piezoelectric Mediated Remineralization," Acta Microscopica, 2009, 18(3):278-286.

Glazner et al., "Cost of vaccine administration among pediatric practices," Pediatrics, 2009, 124(Supplement 5):S492-S498.

Graf et al., "In Stimulation of bone growth by implanted FEP electrets and PVDF piezoelectric films," Proceedings 5th International Symposium on Electrets (ISE 5), Heidelberg, 1985, pp. 813-818.

Habibovic, "Strategic directions in osteoinduction and biomimetics," Tissue Engineering Part A, 2017, 23, (23-24), 1295-1296.

Laurencin et al., "Bone graft substitutes," Expert Review of Medical Devices, 2006, 3(1):49-57.

Laurencin et al., "Regenerative engineering," Science translational medicine, 2012, 4(160):160ed9, 4 pages.

Laurencin et al., "Tissue engineering: orthopedic applications," Annual review of biomedical engineering, 1999, 1, (1), 19-46.

Madlon-Kay et al., "Too many shots? Parent, nurse, and physician attitudes toward multiple simultaneous childhood vaccinations," Archives of Family Medicine, 1994, 3(7):610-13.

McHugh et al., Fabrication of fillable microparticles and other complex 3D microstructures, Science, 2017, 357(6356):1138-1142.

McHugh et al., "Single-injection vaccines: Progress, challenges, and opportunities," Journal of Controlled Release, 2015, 219:596-609.

Meng et al., "A Hybrid Inductive-Ultrasonic Link for Wireless Power Transmission to Millimeter-Sized Biomedical Implats," IEEE Transactions on Circuits and Systems—II: Express Briefs, 2017, 64(10):1137-1141.

Narayanan et al., "Poly (lactic acid)-based biomaterials for orthopaedic regenerative engineering," Advanced drug delivery reviews, 2016, 107, 247-276.

Nguyen et al., "Piezoelectric nanoribbons for monitoring cellular deformations," Nature Nanotechnology, 2012, 7:587-593.

Poeggel et al., "Optical Fibre Pressure Sensors in Medical Applications," Sensors, 2015, 15(7):17115-17148.

Rolland et al., "Direct fabrication and harvesting of monodisperse, shape-specific nanobiomaterials," Journal of the American Chemical Society, 2005, 127(28):10096-10100.

Sanni et al., "Inductive and Ultrasonic Multi-Tier Interface for Low-Power, Deeply Implantable Medical Devices," IEEE Transactions on Biomedical Circuits and Systems, 2012, 6(4):297-308.

Shende et al., Micro to nanoneedles: a trend of modernized transepidermal drug delivery system, Artificial Cells, Nanomedicine, and Biotechnology, 2017, 8 pages.

Simonelli et al., "Dissolution rates of high energy polyvinylpyrrolidone (PVP)-sulfathiazole coprecipitates," Journal of pharmaceutical sciences, 1969, 58(5):538-549.

Soltman et al., "Inkjet-printed line morphologies and temperature control of the coffee ring effect," Langmuir, 2008, 24(5):2224-2231.

Sullivan et al., "Dissolving polymer microneedle patches for influenza vaccination," Nature medicine, 2010, 16(8):915-921.

Tanimoto et al., "Effect of helix inversion of poly(β-phenethyl l-aspartate) on macroscopic piezoelectricity," Japanese Journal of Applied Physics, 2014, 53(9S):09PC01.

Vaers, Vaccine Adverse Event Reporting System. <https://vaers.hhs.gov/data/index> webpage available as early as Oct. 9, 2009, 2 pages.

Xu et al., "Future of the particle replication in nonwetting templates (PR.INT) technology," Angewandte Chemie International Edition, 2013, 52(26):6580-6589.

Yu et al., "Oral fast-dissolving drug delivery membranes prepared from electrospun polyvinylpyrrolidone ultrafine fibers," Nanotechnology, 2009, 20(5):055104, 9 pages.

International Search Report and Written Opinion for Application No. PCT/US2019/020838 dated Jun. 26, 2019 (14 pages).

Ando et al., "Pressure-sensitive touch panel based on piezoelectric poly (l-lactic acid) film", 2013, Jpn. J. Appl. Phys. 52:09KD17.

Bello et al., "Development of a smart pump for monitoring and controlling intraocular pressure", Ann Biomed Eng 45:990-1002, 2017.

Bos et al., "Resorbable poly(L-lactide) plates and screws for the fixation of zygomatic fractures", 1987, J Oral Maxillofac Surg, 45:751-753.

Chee et al., "An investigation of array of piezoelectric transducer for raindrop energy harvesting application", 2016, IEEE Region Tenth Conference, pp. 3771-3774.

Lee et al., "Micromachined piezolectric force senors based on PZT thin films", 1996, IEEE Trans Ultrason Farroelectri Freq Control, 43:553-559.

Di Mario et al., "Drug-eluting bioabsorbable magnesium stent", 2004, J Interv Cardiol., 17:391-395.

Fukada, "New Piezoelectric polymers" 1998, Jpn J Appl Phys 37:2775-2780.

Ewald et al., "Monitoring of vital signs for long-term survival of mice under anesthesia", 2011, Cold Spring Harb Protoc. 2011:pdb.prot5563.

Guo et al., "Measurements of piezoelectric coefficient d33 of lead zirconate titanate thin films using a mini force hammer", 2013, J Vib Accoust, 135:011003.

Jayson et al, "Intra-articular pressure in rheumatoid arthritis of the knee 3. Pressure changes during joint use", Ann Rheum Dis, 1970, 29:401-408.

(56) References Cited

OTHER PUBLICATIONS

Kang et al., "Bioresorbable silicon electronic sensors for the brain", Nature, 2016, 530:71-76.
Liu et al., "Design and development of three-dimensional scaffolds for tissue engineering", 2007, Chem Eng Res Des, 85:1051-1064.
Maloney et al., "Intracranial pressure monitoring in acute liver failure: Institutional case series", 2016, Neurocrit Care 25:86-93.
Ando et al., "Film sensor device fabricated by a piezoelectric poly(L-lactic acid) film", 2012, Jpn J Appl Phys 51:09LD14.
Minary-Jolandan et al., "Nanoscale characterization of isolated individual type I collagen fibrils: Polarization and piezoelectricity", 2009, Nanotechnology 20:085706.
Nguyen et al., "Wafter-scale nanopatterning and translation into high-performance piezoelectric nanowires", 2010, Nano Lett 10: 4595-4599.
Nguyen, et al., "Bionics in tissue engineering" 2017, Tissue Engineering for Artifical Organs, pp. 677-669.
Qi et al., "Enhanced piezoelectricity and stretchability in energy harvesting devices fabricated from buckled PZT ribbons", 2011, Nano Lett. 11:1331-1336.
Ru et al., "Dominant B-form of poly(l-lactic acid) obtained directly from melt under shear and pressure fields", 2016, Macromolecules 49:3826-3837.
Saravanos et al., "Layerwise mechanics and finite element for the dynamic analysis of piezoelectric composite plates", 1997, Int J Solids Struct 34:359-378.
Sawano et al., "New design of actuator using shear piezoelectricity of a chiral polymer, and prototype device", 2010, Polym. Int. 59: 365-370.
Seol et al., "Hysteretic behavior of contact force response in triboelectric nanogenerator", 2017, Nano Energy 32:408-413.
Sinderby et al., "Diaphragm activation during exercise in chronic obstructive pulmonary disease", 2001, Am J Respir Crit Care Med, 163:1637-1641.
Syuhei et al., "Sensing using piezoelectric chiral polymer fiber", 2012, Jpn. J. Appl. Phys. 51:09LD16.
Tajitsu et al., "Microactuators with piezoelectric polylactic acid fibers—toward the realizaation of tweezers for biological cells", 2004, Ferroelectrics 304:195-200.
Talmor et al., "Mechanical ventilation guided by esophageal pressure in acute lung injury", N. Engl. J Med., 2008, 359, 2095-2104.
Xu et al., "Improvements of thermal property and crystallization behavior of PLLA based multiblock copolymer by forming sterocomplexwith PDLA oligomer", 2006, Polymer (Guildf), 47:3922-3928.
Yoshida et al., "High piezoelectric performance of poly (lactic acid) film manufactured by solid state extrusion", 2014, Jpn. J. Appl. Phys. 53:09PC02.
Yoshida et al., "Piezolectric motion of multilayer film with alternate rows of optical isomers of chiral polymer film", 2011, Jpn J Appl Phys 50:09ND13.
Zheng et al., "Biodegradable triboelectric nongenerator as a lifetime designed implantable power source", 2016, Sci Adv 2:e1501478.
Zi et al., "Triboelectric-pyroelectric-piezoelectric hybrid cell for high-efficiency energy-harvesting and self-powered sensing", Adv Mater 27:2340-2347, 2015.
D'Lima et al. "Implantable sensor technology: measuring bone and joint biomechanics of daily life in vivo", Arthritis Reseasrch and Therapy, 2013, 15: 203.
Klosterhoff et al., "Implantable Sensors for Regenerative Medicine", Journal of Biomechanical Engineering, ASME Feb. 2017, vol. 139, 021009-1.
International Preliminary Report on Patentability for Application No. PCT/US2018/022441 dated Sep. 17, 2019 (10 pages).
Boutry et al., "A sensitive and Biodegradable Pressure Sensor Array For Cardiovascular Monitoring", Advanced Materials, 27, 2015, pp. 6954-6961.
International Search Report and Written Opinion for Application No. PCT/US2018/022441 dated Aug. 1, 2018 (12 pages).
Zhang et al., "Piezoelectric polymer multilayer on flexible substrate for energy harvesting," IEEE Transactions on Ultrasonics, Ferroelectrics, and Frequency Control, 2013, 60(9):2013-2020.
Ramadan et al., "A review of piezoelectric polymers as functional materials for electromechanical transducers," Smart Materials and Structures 23, 2014, 033001.
Dagdeviren et al., "Recent progress in flexible and stretchable piezoelectric devices for mechanical energy harvesting, sensing and actuation," Extreme Mechanics Letters, 2016, 9(1):269-281.
European Patent Office Extended Search Report for Application No. 18767093.0 dated Nov. 27, 2020 (13 pages).
European Patent Office Extended Search Report for Application No. 19764864 dated Mar. 22, 2022 (11 pages).

\* cited by examiner

BIODEGRADABLE PIEZOELECTRIC NANOFIBER SCAFFOLD FOR BONE OR TISSUE REGENERATION

CROSS-REFERENCE TO RELATED APPLICATIONS

This application is a non-provisional of and claims the benefit of U.S. Provisional Patent Application No. 62/812,499, filed on Mar. 1, 2019, the contents of which are incorporated herein by reference.

COLOR DRAWINGS

The patent or application file contains at least one drawing executed in color. Copies of this patent or patent application publication with color drawings will be provided by the Office upon request and payment of the necessary fee.

BACKGROUND

Reconstruction of large or major bone, nerve, skin, cartilage, and muscle defects remains a significant challenge in modern medicine. Worldwide, for bone alone, 20 million people, including soldiers and military personnel, suffer from a loss of bone tissue annually. In the U.S. alone, over half a million bone-defect repairs occur every year, costing more than 2.5 billion dollars. Until now, the golden treatment is to use auto- or allo-grafts, which suffer from limited supply, donor site morbidity, infection, and/or immune-rejection.

Regenerative and tissue engineering strategies which aim to create artificial "engineered" tissue grafts have therefore emerged as an important area. In the construction of such bone grafts, biomaterial scaffold plays a significant role. For design categories, these scaffolds need to be (1) biodegradable to facilitate formation of new bone and avoid invasive removal surgery, (2) possess properties similar to that of native bone tissues, (3) compatible with seeded cells, and (4) capable of carrying stimulation factors, which induce osteogenesis.

Bone growth factors and small molecules have been extensively studied for osteoinduction (i.e., to induce bone formation), but many of their toxic side effects demand for a new approach to stimulate bone growth. Bioelectricity is an inherent signal of living organisms, and electrical factors (e.g., current, voltage, charge etc.) can stimulate healing of tissues, especially bones. Electrical stimulators have been used to treat bone fractures and accelerate bone healing. Yet, clinical application of these devices is still limited. While external electrical stimulators are not effective enough, implanted devices often rely on toxic batteries, percutaneous wires and are non-degradable, requiring invasive surgery for removal. Thus, there is a critical need to develop a new approach, effectively utilizing electrical stimulation in combination with biomaterial scaffolds and stem cells, to promote bone regeneration for healing large-scale bone defects.

SUMMARY

Ultrasound is a common non-invasive therapeutic method, clinically used to treat bone defect. Ultrasound with low intensity and low frequency can avoid a heating effect on the treated tissues. Especially, low-intensive pulse ultrasound (LIPUS) has been shown to promote bone-fracture healing. LIPUS alone, however, is only effective at the early phase of bone formation, and limited to treat small-scale bone defects.

This disclosure provides a novel biodegradable piezoelectric polymer of PLLA that provides a solution to construct an ideal biodegradable piezoelectric tissue scaffold. Ultrasound parameters are evaluated and selected to produce sufficient surface charge on the PLLA piezoelectric scaffold, inducing osteogenic differentiation of seeded stem cells. By combining the effects of surface charge and the ultrasound, it is believed to significantly enhance regeneration and healing of large-scale bone defects. The disclosure describes a novel and transformative strategy, relying on non-invasive and wireless electrical-stimulation to offer a powerful platform technology for tissue regeneration.

For bone repair, the approach is significant for clinical use with multiple advantages. First, the tissue scaffold relies on common medical materials including PLLA polymer and collagen hydrogel, which have been extensively used in many FDA-approved implants and bone tissue constructs. These materials have been shown to be biocompatible and to biodegrade over time, facilitating formation of new bone. Second, nanofibers of PLLA are known to simulate extracellular matrix (ECM), offering an excellent scaffold to home osteogenic cells. Third, adipose-derived stromal/stem cells (ASCs) are utilized, which can be harvested in a minimally-invasive liposuction on subcutaneous fat of patients and easily expanded in vitro. And fourth, to generate acoustic pressure, non-invasive ultrasound is employed, which is also a common method to accelerate bone healing in clinics. By controlling the ultrasound and designing the scaffold properly, the surface charge can be engineered and regenerative capability of the proposed engineered tissue-construct can be optimized. Collectively, this novel piezoelectric tissue graft can transform and offer a significant impact on the field of bone repair and tissue regeneration.

The embodiments described herein provide (1) a wireless and non-invasive ultrasonic technology to generate electrical stimulation for inducing tissue and bone growth, (2) a tool to systematically study interaction between stem-cells and surface charge for bone regeneration, and (3) an approach to design and create a novel 3-D biodegradable piezoelectric biomaterial scaffold which can be seeded with stem cells to form highly-regenerative replacement artificial bone grafts. As nerve, muscle, skin, cartilage, etc. can be healed under electrical stimulation, the scaffold and the stimulation method can be used to repair various tissue defects, offering a powerful platform technology for tissue regeneration.

In one embodiment, the disclosure provides a method of regenerating bone or tissue. The method comprises applying a scaffold to a wound, the scaffold comprising a plurality of PLLA layers, each layer separated by a hydrogel layer, applying ultrasound energy to the scaffold, generating an electrical surface charge on the scaffold, and delivering an electrical output to the bone or tissue from the scaffold to regenerate the bone or tissue.

In another embodiment, the disclosure provides a scaffold for regenerating bone or tissue. The scaffold comprises a plurality of PLLA layers comprising a nanofiber mesh, the PLLA layers having a piezo constant of 15-20 pC/N, and a plurality of hydrogel layers, each hydrogel layer positioned between two PLLA layers. The plurality of PLLA layers deliver an electric charge to the bone or tissue after ultrasound energy is applied to the plurality of PLLA layers to induce growth of the bone or tissue.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Piezoelectricity is a phenomenon which allows materials to convert deformation into electricity and vice versa. Piezoelectric materials are often used for force/pressure sensors, transducers, and generators. The materials can be fabricated into nano- and microstructures and interfaced with soft tissues to monitor biological forces. Since piezoelectric materials can generate electricity from mechanical impact, they can serve as appealing sensing materials, alternative to the described passive semiconductors and capacitive polymers, for self-powered force sensors. However, commonly used piezoelectric materials such as lead zirconate titanate (PZT) and polyvinylidene difluoride (PVDF) contain toxic or non-biodegradable components, respectively, and thus are not favorable for implantation inside the human body. Poly-L-lactic acid (PLLA), a biodegradable polymer used extensively in FDA-approved implants, has recently been found to exhibit piezoelectricity when appropriately processed. The material exhibits shear piezoelectricity due to electrical polarity present in the carbon-oxygen double-bond branching off from the polymer backbone chain. Although possessing a modest piezoelectric response (5-15 pC/N), PLLA has a low dielectric constant, which allows the material to perform the same energy-conversion efficacy as the common piezoelectric polymer PVDF. By creating multilayers, one can achieve even higher piezoelectricity from PLLA, with an "effective" conversion efficiency, similar to that of ceramic PZT.

The biodegradable piezoelectric scaffold disclosed herein may be constructed from processed biocompatible polymers, such as poly-lactic acid (PLA), poly-lactic glycolic acid (PLGA), and the like.

Figure 1:
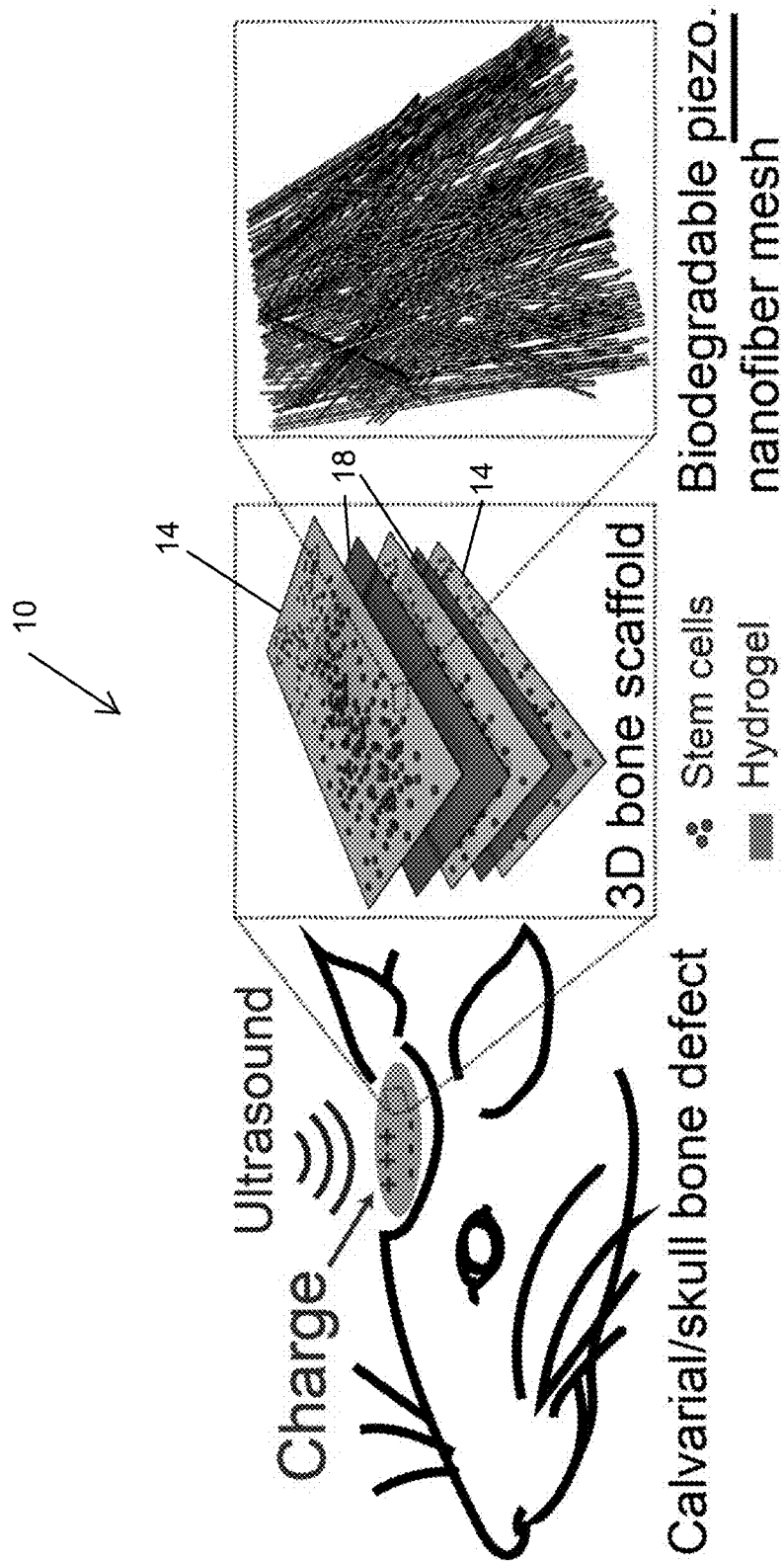
FIG. 1 illustrates 3D biodegradable piezoelectric PLLA-nanofiber scaffold, seeded with stem cells, to treat, for example, calvarial/skull bone defect. Under ultrasound, acoustic pressure is induced on the PLLA piezoelectric nanofibers to produce surface charges which enhance osteogenesis of the stem cells, and bone regeneration for a calvarial bone defect in mice.

FIG. 1 illustrates a scaffold 10 comprised of a plurality of PLLA layers 14. The PLLA layers 14 may include stem cells as shown. The PLLA layers 14 are separated by a plurality of hydrogel layers 18. In one construction, the scaffold 10 comprises a disc-like shape of ~4 mm in diameter, and 0.5 mm in depth and is configured to match with the critical-size calvarial defect for mice in an in vivo experiment. This construction provides that each of the PLLA layers 14 is about 25 μm thick and each of the hydrogel layers 18 is about 10-25 μm thick. The scaffold 10 may comprise about 2-10 PLLA layers 14. The PLLA layers 14 comprise a nanofiber mesh, which is made by different collector rotation speeds (1,000-4,000 rpm) of an electrospin process to exhibit different piezoelectric constants (i.e., efficiency to convert mechanical loading to output charge).

Electrospinning is used to create the nanofiber mesh of the PLLA layers 14. The polymer is dissolved in a mixture of Dimethylformamide (DMF) and Dichloromethane (DCM) (1:4) and then injected through a metal needle onto a conducting collector drum under an application of high electrical field (1 kV/cm). The electrospin system utilizes a drum that is rotated at a very high speed (1,000-4,000 rpm) to mechanically stretch and align the nanofibers (Eli Curry et al., Biodegradable Piezoelectric Nanofiber Based Transducer, PNAS Jan. 7, 2020 117 (1) 214-220). Additionally, the PLLA layer is post-treated by thermal annealing at sequential temperatures of 130° C. and 160° C. before slowly cooling down the samples to room temperature.

To evaluate piezoelectric effect of the PLLA, two methods are employed; first, the electrospun (Espun) PLLA nanofiber layer is subject to a known mechanical force, and voltages generated from the PLLA layers (impact mode) are measured. Impact force is used because it is more controllable than ultrasound to assess piezoelectric performance of the PLLA. Second, a known electrical field is applied on the layers and a laser displacement sensor is used to measure vibration or deformation of the layer via the converse piezoelectric effect (vibration/actuation mode). Using a reported model for shear-piezoelectricity in PLLA and the experimental results, a piezoelectric constant ($d_{14}$) of each Espun PLLA nanofiber mesh is quantified, which determines the efficiency to convert applied force into output charge (pC/N).

The piezoelectric Espun PLLA nanofiber layers are sterilized (ethanol+UV light) and placed onto a petri-dish for cell seeding. Adipose-derived stromal/stem cells (ASCs) (104-105 cells/cm$^2$) are seeded onto the layer and it takes 2-3 days for the cells' attachment and proliferation on the layer surface. The PLLA can also be bonded with a layer of collagen, loaded with calcium phosphate such as tri-calcium phosphate (TCP), to increase osteoconductivity. The layers are then collected and bonded together by using adhesive and biocompatible collagen hydrogel, which has been used commonly in bone scaffolds. For the in vitro experiment, ASCs from a commercial source (mouse cells, 10MU-006, iXCells Inc.) were used. For the in vivo experiment, ASCs from subcutaneous fat tissue of the animals were collected. To perform the bonding, collagen solution (kept at 4° C.) was neutralized and casted on top of each cell-seeded PLLA layer. The second PLLA layer was placed on top of this thin gel layer. The hydrogel was cured at 37° C. after 20-30 minutes, bonding the two PLLA layers together. The same process was repeated to create more layer structure until a 3D scaffold with a desired thickness was obtained.

Figure 2:
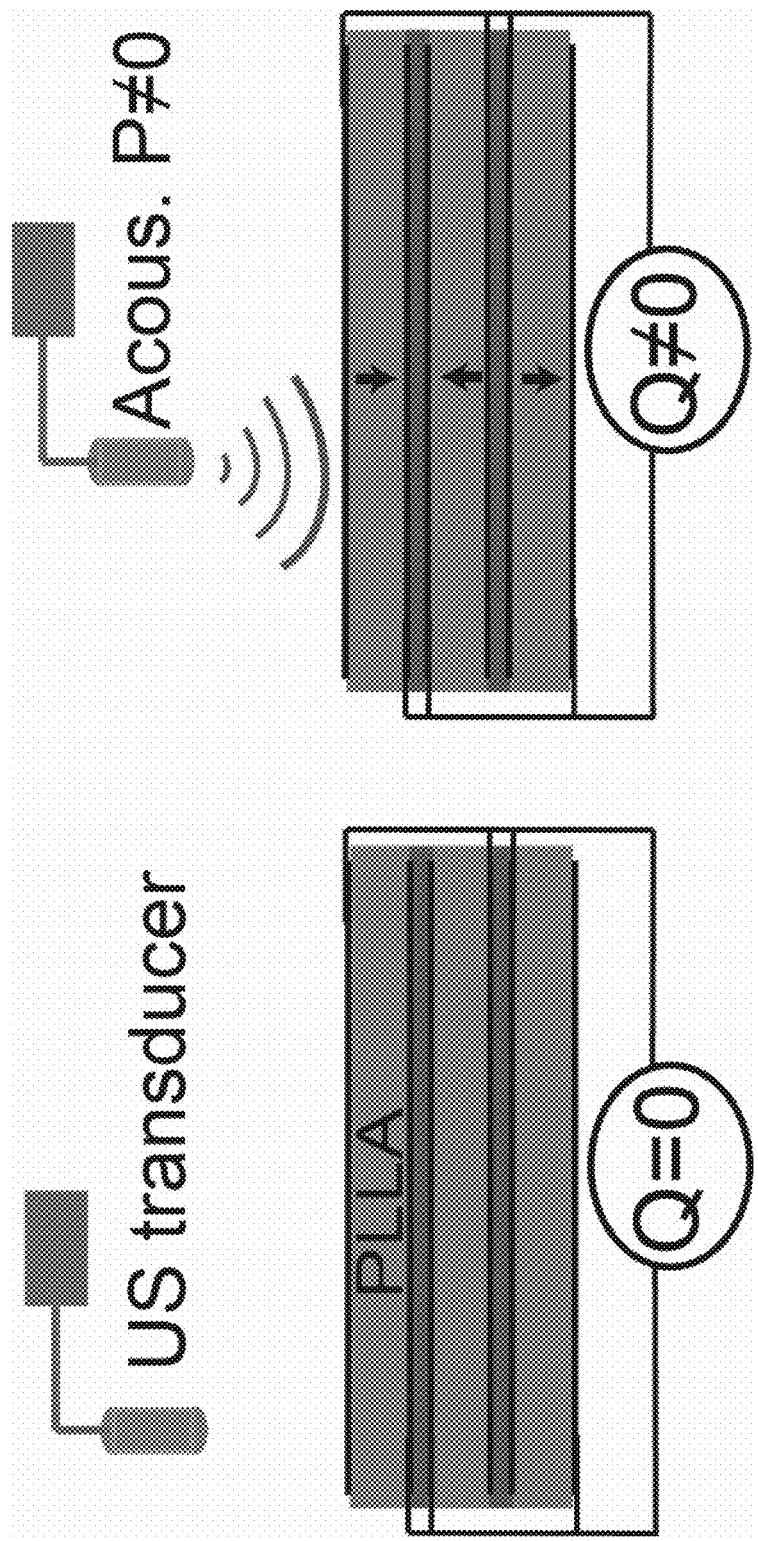
FIG. 2 illustrates a schematic assessment of charge output from applied acoustic pressure (acous. P). Red=hydrogel, green=PLLA, black=encapsulated electrodes.

To quantify surface charge, generated from the scaffold under applied ultrasound, electrodes were deposited on each PLLA layer. The electrodes were encapsulated by PMMA (Polymethylmethacrylate), and the electrode/PLLA layers were assembled into the 3D scaffold. All positively-charged surfaces of the PLLA layers were electrically connected together and all negatively-charged surfaces were wired together as shown in FIG. 2. The surface charge or polar direction of each PLLA layer was identified by observing polarization of peak-voltage from each layer under impact force (see preliminary data in FIG. 3). The scaffold (without stem cells) was then placed inside culture medium and the scaffold was exposed to different acoustic pressures by varying ultrasound intensity. To induce the ultrasound, a commercial ultrasound transducer (e.g., Bolt Clamped Langevin Transducer) was used. The electrodes of the scaffold were connected to an electrometer which provided output charge. The experiment was performed inside a Faraday cage to avoid electrostatic noise.

The ultrasound generated different surface charges from different 3D piezoelectric PLLA scaffolds, made of different numbers of PLLA layers (i.e., 2, 4, 6, 8 and 10 layers) and from PLLA layers, made by different spin-speeds of the drum-collectors (i.e., 1,000, 2,000, 3,000 and 4,000 rpm). While changing the number of PLLA layers, the thickness of the hydrogel layers was tailored to keep the entire thickness of the scaffold constant (~500 µm). For each scaffold, different ultrasound intensities (10-400 mW/cm$^2$, 40 kHz) were applied for 30 minutes/day and 5 days/week over a period of 20 days. The frequency to simplify the experiment was fixed and the ultrasound intensity was controlled to engineer surface charges. The surface-charge from daily stimulation was recorded, and how the charge varied over the course of time was assessed.

Figure 3:
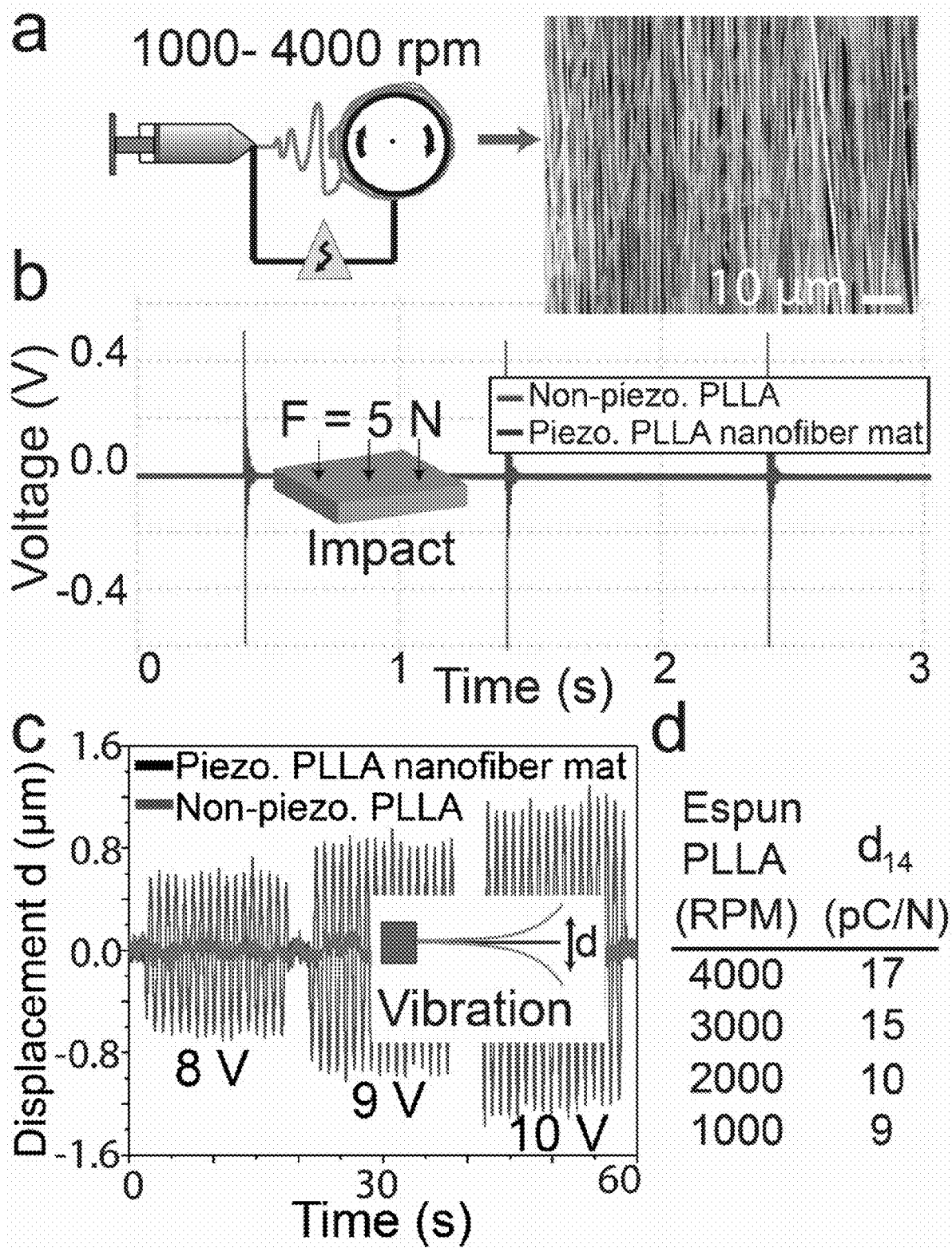
FIG. 3 illustrates preliminary data on fabrication and characterization of the piezoelectric PLLA nanofiber mesh. a. Electrospin system (left) and SEM of fabricated PLLA nanofiber mesh. b. Voltage outputs from PLLA layers under impact force of 5 N. c. Vibration of the layers (measured by laser-displacement sensor) under applied AC voltages with different magnitudes (freq. ~1 Hz). d. Piezoelectric constants of the PLLA nanofiber samples, made by different spin speeds of the collector drum.

Fabrication of the PLLA piezoelectric nanofiber mesh: highly-aligned PLLA nanofibers were achieved, using the aforementioned electrospinning system (see FIG. 3 (at a)). The PLLA nanofibers were obtained with a high degree of crystallinity (~70-80%), crystal-alignment (Herman factor of ~0.9) and a stable crystal phase (β-phase). These properties were assessed by using X-ray diffraction (XRD) and differential scanning calorimetry (DSC). The treated Espun PLLA layer was able to provide a distinct voltage output, compared to a non-piezoelectric PLLA layer, under the same impact force (see FIG. 3 (at b)). Receiving the AC voltage input, the Espun layer deforms and vibrates with the same frequency of the input voltage while a non-piezoelectric PLLA layer has no movement under the same condition (see FIG. 3 (at c)). It can be seen that a higher drum speed (i.e., more aligned PLLA nanofibers) increases the piezoelectricity of the PLLA nanofiber mesh (see FIG. 3 (at d)). Compared to previously-reported piezoelectric PLLA solid layer ($d_{14}$~11 pC/N), the Espun nanofibers exhibit superior piezoelectricity. The piezo-constant ($d_{14}$) of the Espun PLLA mesh with drum-speeds of 3,000 and 4,000 rpm are almost 20 pC/N, among the highest piezoelectric constants for polymers (e.g., PVDF is ~15-20 pC/N). Using higher spin-speed of the collector, piezoelectric performance can be increased. Yet, higher spin speed would create an extremely-anisotropic PLLA nanofiber mesh, making the PLLA layer very fragile and mechanically unstable. Therefore, spin-speeds in a range of 1,000-4,000 rpm can be utilized to fabricate the bone scaffolds.

Figure 4:
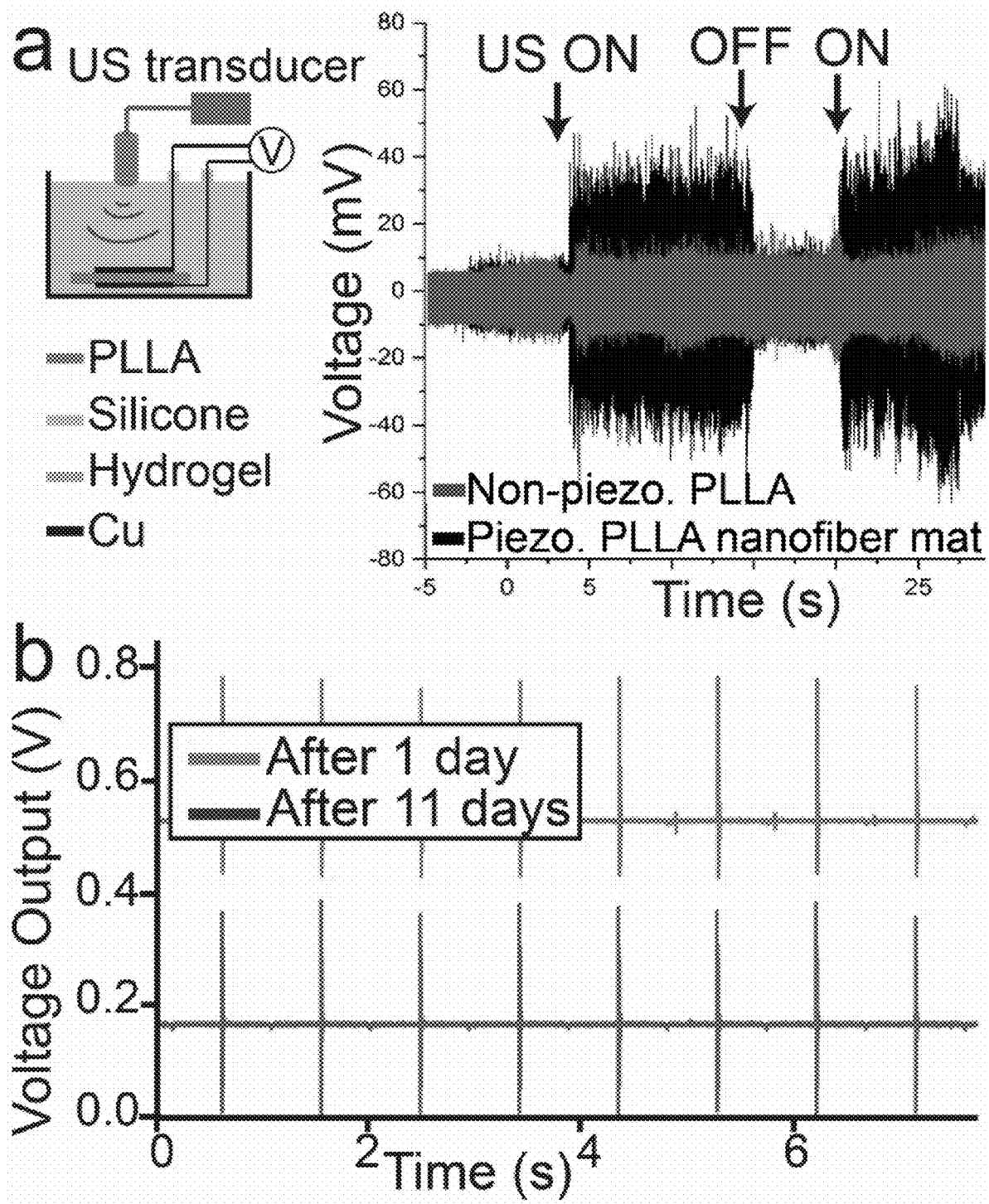
FIG. 4 illustrates a response of the PLLA nanofiber layer to ultrasound and stability of piezoelectric output. a. Signal response from the PLLA layers inside a hydrogel/aqueous medium, to ultrasound. b. Consistent voltages, generated from the same impact forces, on a piezo-PLLA nanofiber layer after 11 days.

Response of the PLLA nanofiber layer to applied ultrasound and piezoelectric stability: the ability of the Espun PLLA layer to produce electricity or surface-charge under applied acoustic-pressure has been verified. The layers with encapsulated electrodes on two major surfaces were placed inside a collagen hydrogel (see FIG. 4 (at a—left side)). An acoustic wave of 0.2 W/cm$^2$ at 40 kHz was applied. It was discovered that the piezoelectric PLLA nanofiber layer provides a significant electrical signal, while a non-piezoelectric PLLA layer (untreated PLLA) in the same condition only generates noise (see FIG. 4 (at a—right side)). Furthermore, to test the stability of piezoelectricity, the Espun layer was incubated inside a culture medium at 37° C. The layer had two encapsulated electrodes but itself was completely exposed to the medium. The same mechanical force was applied onto the layer after and before the incubation. As seen in FIG. 4 (at b), the Espun layer exhibited a consistent output voltage under the same impact force after 11 days of incubation. This stability is useful for a lengthy process of culturing cells and implantation in later experiments. This stability was attributed to the stable crystal-phase and high degree of crystallinity in the thermally-treated PLLA nanofiber layers. Note that highly crystalline PLLA still erodes with a low degradation rate and thus is still favorable to serve as a biodegradable bone scaffold.

A wide range of ultrasound parameters and scaffold designs might be difficult for selection at the beginning. Previous works have shown that PVDF or Hydroxyapatite (HA), polarized under a high electrical field (2-10 kV/cm) to possess inherent surface charge, can promote osteogenic differentiation of stem cells and enhance bone regeneration. The inventors can create such materials, measure their surface-charge, and use this charge value as a reference for selecting appropriate scaffold-designs and ultrasound stimulations at the beginning.

Osteogenesis from the 3D piezoelectric PLLA nanofiber scaffolds, seeded with stem cells under acoustic loading of applied ultrasound in vitro was studied.

Experimental design: the 3D cell-seeded PLLA scaffold was placed into a petri-dish filled with medium and acoustic pressure was applied on the scaffolds (same as FIG. 4 (at a—left side). To facilitate osteogenic differentiation in vitro, the scaffolds were cultured in a typical osteogenic differentiation medium (ODM). Table 1 describes five major experimental groups (n=6 scaffolds/group, see statistical analysis), for the in vitro study. The ultrasound intensity, scaffold design, and piezoelectric constant of the PLLA layer was varied. Therefore, each major group had several sub-groups. By comparing between the five major groups, the inventors were able to rule out the effect of ultrasound or the piezoelectric scaffold alone, and demonstrate the need of the combination to generate piezoelectric charge, which drives osteogenic differentiation of the stem cells. For group #5, BMP-2 in the range of 20-100 ng/ml was used which has been histologically used to induce osteogenic differentiation of cells in vitro. In groups #2 and #4, different PLLA scaffolds, made of different layer numbers and PLLA layers with different piezoelectric constants, was used. The inventors investigated how the seeded cells on each scaffold performed osteogenic differentiation and compared the outcomes between different groups.

TABLE 1

Designed groups for in vitro study

| Group | Medium | Condition | Note |
|---|---|---|---|
| 1 | Regular | ASC + Non-piezo. PLLA Scaffold | Negative control |
| 2 | ODM | ASC + piezo. PLLA scaffold + US | Exp. group |
| 3 | | ASC + Non-piezo. PLLA scaffold + US | Sham |
| 4 | | ASC + piezo. PLLA scaffold | Sham |
| 5 | | ASC + Non-Piezo. PLLA scaffold + BMP | Positive Control |

Selecting ultrasound parameters: With groups #2 and #3, the ultrasound intensity (in the range of 10-400 mW/cm$^2$, measured by a hydrophone) was varied to generate different surface charges. This intensity range (<0.5 W/cm$^2$) was selected because it is commonly used in ultrasound therapy for bone healing. To simplify the experimental design, the frequency was fixed at 40 kHz. Low-frequency ultrasound (in kHz range) has been shown to penetrate tissues better than the high-frequency ones (in MHz range) and also avoid heating effect on organs/tissues. The ultrasound was applied 30 minutes/day and 5 days/week for 20 days. The periods of ultrasound application were selected based on previous research of using ultrasound for bone regeneration. This time frame was also reasonable to mitigate stress on animals and reduce labor intense to perform the stimulation. Confirmed by the data (see FIG. 4 (at a—right side)), the ultrasound in this range can generate significant electrical outputs (i.e., surface charge) on the piezoelectric PLLA scaffold to induce osteogenesis.

Assessing osteogenic differentiation: At each time point (7, 14, 28 and 42 days, similar to previous works), (1) cell viability, (2) cell proliferation, (3) cell differentiation by gene expression, (4) enzymatic-activity, and (5) mineralization of the cultured scaffolds were assessed.

Briefly, cell viability kits (MTT or 3-(4,5-Dimethylthiazol-2-yl)-2,5-diphenyltetrazolium bromide for assay and live/dead assay) were carried out to quantify proliferation of cells along with number of healthy cells. To assess osteogenic differentiation, enzymatic activity of alkaline phosphastase (ALP) was quantified by colorimetric assays. mRNA expression of typical osteogenic markers (runx2, osterix, collagen I, osteocalcin, and osteopontin) and pro-angiogenic markers (HIF-1α, PDGF, angiogenin, angiopoetin-1, and angiopoetin-2) was quantified, using real time polymerase chain reaction RT-qPCR. Matrix mineralization was assayed by alizarin red stain. Optical readings were obtained and intensity of the staining was quantified in each assay. All readings were normalized to the protein concentration or cell number of each culture sample. Outcomes from the piezoelectric scaffolds (group #2) were statistically compared to other groups using student paired t-test. Oil-red O to stain lipid was also employed to verify that the ASCs would not turn into mature adipose cells.

Figure 5:
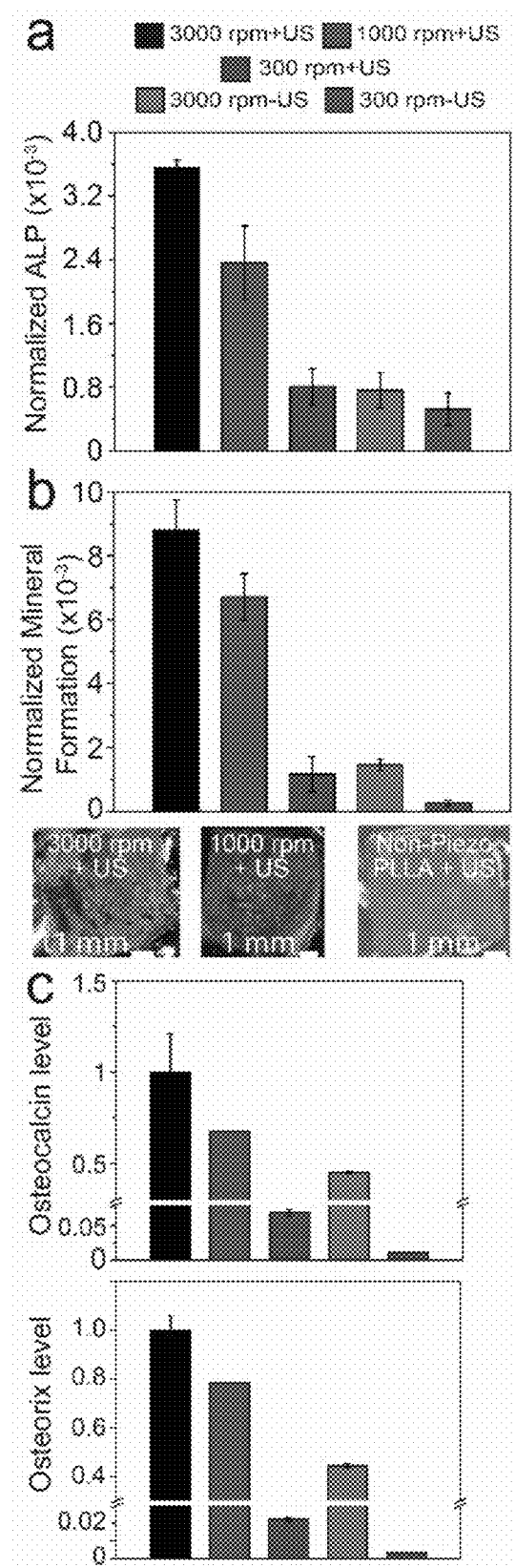
FIG. 5 is preliminary data on osteogenesis of ASCs seeded on the Piezo-PLLA scaffold under applied acoustic pressure. a. ALP activity. b. Top is the quantified mineralization from Alizarin red staining. Bottom are optical images of different scaffolds stained by Alizarin red. c. RT-qPCR results on expression of osteogenic genes from ASCs, cultured on different piezo-scaffolds under the same ultrasound and normal tissue culture plate (TCP, negative control). Student t-test with *$p<0.05$, $p<0.01$, and *$p<0.001$. (n=3 for each assay).

Experimental data: the ASCs on the constructed PLLA scaffold were seeded in ODM and the scaffolds exposed to ultrasound (0.3 W/cm$^2$, 40 KHz, 30 minutes/day, 5 days a week for 10 days). Two piezoelectric scaffolds were used with the same dimensions and made of two PLLA nanofiber layers with drum speeds of 1,000 rpm and 3,000 rpm. These two layers generated different surface charge under the same ultrasound. FIG. 5 (at a) shows that the scaffold with more piezoelectric effect (i.e., 3,000 rpm) exhibits higher ALP activity than the ones with less piezoelectric effect (i.e., 1,000 rpm) and non-piezoelectric effect (i.e., non-treated PLLA). Without the applied ultrasound, the 3,000 rpm PLLA scaffold induces very little ALP because the PLLA layer doesn't have any spontaneous surface charge. Non-piezoelectric scaffolds with the applied ultrasound induces better ALP activity than that of the piezoelectric scaffold without applied ultrasound. Alizarin red was used to stain mineral formation. As seen in FIG. 5 (at b), similar to the ALP, the scaffold of 3,000 rpm PLLA layers exhibits a superior mineralization, compared to the 1,000 rpm scaffolds and the non-piezoelectric scaffolds under the same ultrasound. Optical images also indicate more visible red staining (i.e., more mineralization) on the 3,000 rpm scaffold, compared to the less-piezoelectric (1,000 rpm) and non-piezoelectric scaffolds under the same condition. Using RT-qPCR, the expression of two osteogenic genes (osteorix and osteocalcin) of the ASCs after 21-day culture was quantified. Consistent with the results of ALP and Alizarin-red assays, FIG. 5 (at c) shows that the 3,000 rpm scaffolds are more osteogenic than the 1,000 rpm scaffolds under the same ultrasound. The 3,000 rpm scaffolds without ultrasound induce less expression of osteorix and osteocalcin from the ASCs.

Besides ASCs, the ability of the piezoelectric scaffold under applied ultrasound was tested, to induce osteogenic differentiation of bone marrow stem cells (BMSCs). These cells are special transgenic cells which can exhibit green fluorescence when differentiating into osteoblasts (early bone formation marker) and red fluorescence when differentiating into osteocytes (later bone formation marker).

The cells were harvested from transgenic mice, provided by the Center for Regenerative Medicine and Skeletal Development at UCHC. The transgenic mice, as described in a previous work, highly express BSP (bone sialoprotein, green fluorescence) and DMP1 (dentin matrix protein, red fluorescence) in osteoblasts and osteoclast, respectively.

Thus, the BMSCs from these mice can be used as excellent fluorescent reporters for osteogensis. The inventors have seeded the same amount of the reported cells onto different scaffolds (3,000 rpm, 1,000 rpm and non-piezoelectric scaffold) and applied the same acoustic pressure, as used in the previous experiment for ASCs. The red- and green-fluorescent signals between cells grown on the higher-piezoelectric scaffolds (3,000 rpm) and those grown on less-piezoelectric scaffold (1,000 rpm) as well as non-piezoelectric PLLA to assess the effect of surface charge on osteogenesis were compared.

Figure 6:
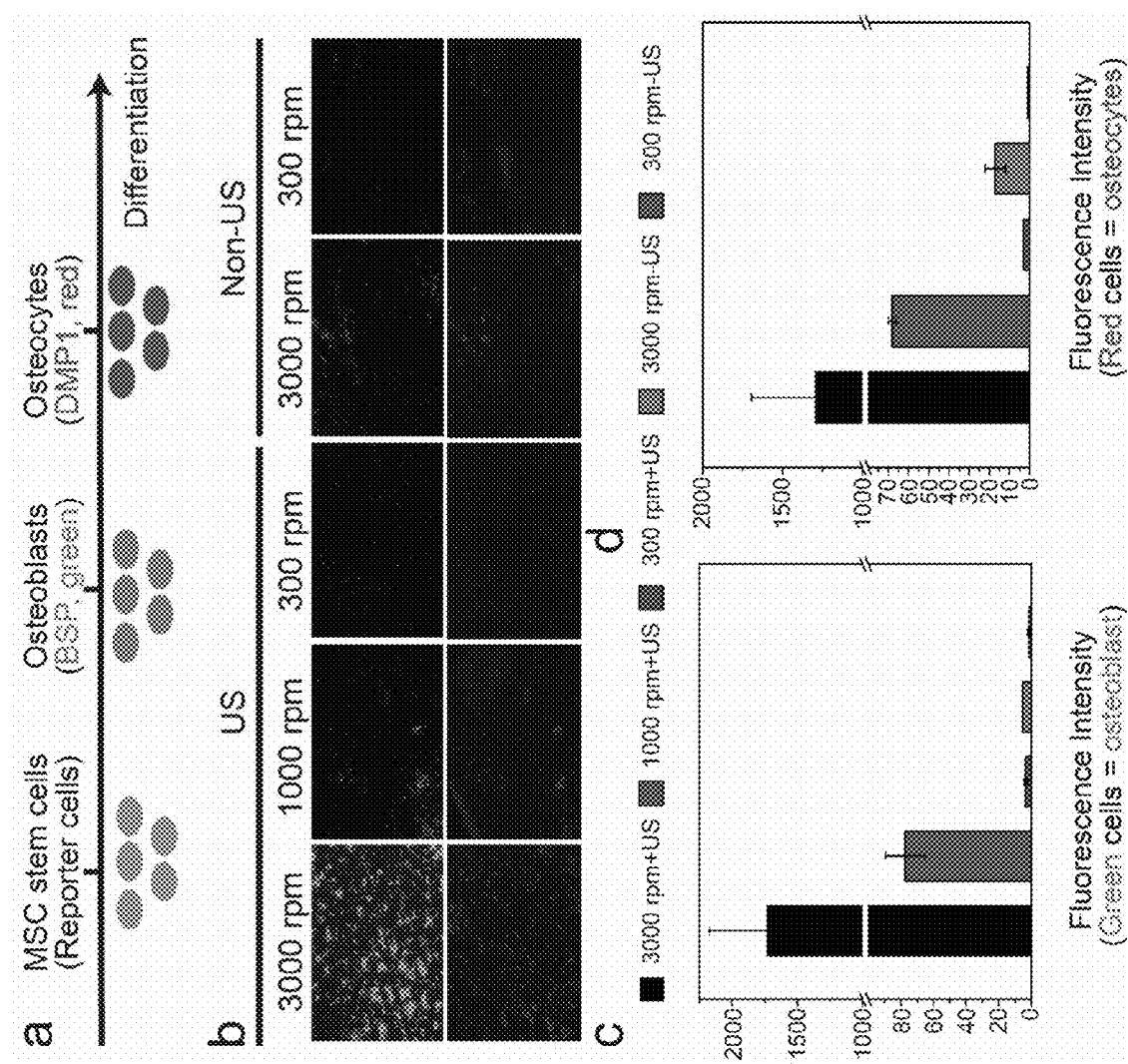
FIG. 6 illustrates osteogenesis of reporter stem cells (MSCs) grown on piezoelectric scaffolds under ultrasonic application. a. Scheme to describe how the reporter cells will express BSP (green) and DMP1 (red) signals when differentiated into osteoblasts and osteoclasts. b. Optical images of the reporter cells after 5 days of applied ultrasound show a superior green and red signals from the piezoelectric scaffold (3000 rpm) to other groups under the same applied ultrasound. (c, d) are quantified fluorescence signals from the cells grown on different groups, again demonstrating a high osteogenesis of the 3000 rpm PLLA scaffold, which generates higher surface charge, compared to the other groups, under the same ultrasound.

As seen in FIG. 6, after 5 days of culturing, the piezoelectric nanofiber scaffolds under applied ultrasound generated superior osteogenesis, compared to the other control and sham groups. This can be seen through a great number of both green and red reporter cells, appeared on the piezo-scaffolds (i.e., 3,000 rpm scaffold) under ultrasound. Similar to the result for ASCs, the 3,000 rpm scaffold exhibit much higher green and red fluorescence signals than the 1,000 rpm one under the same applied ultrasound, indicating that higher surface-charge produces more osteogenesis from the BMSCs. Without the applied ultrasound (i.e., non-ultrasound groups), there was not much osteogenesis (i.e., not much green or red cells) on the piezoelectric 3,000-rpm scaffold because the scaffold didn't possess a spontaneous surface charge without applied pressure.

These data together illustrate a clear positive effect of surface charge to induce osteogenesis and enhance bone formation from seeded stem cells. The piezoelectric scaffold under applied ultrasound indeed induces a significant osteogenic differentiation from both ASC and MSC stem cells.

Stacking layers of PLLA meshes with small pore sizes (10-100 nm) might prevent the seeded cells from receiving oxygen and nutrition. It is envisioned that larger pores can be created by punching the PLLA electrospun layers with a 30-gauge needle (~150 μm OD tip) before assembling them to construct the 3D scaffold. The preliminary data (FIG. 3 and FIG. 5) have shown a high viability and osteogenesis of the seeded stem cells, thus making this concern less significant.

Enhanced bone regeneration from the proposed cell-seeded piezoelectric PLLA scaffold under applied ultrasound in vivo was studied and demonstrated.

BALB/c mice (~2 months old and immune-deficient for using ASCs from different mice) was used to create the calvarial defect model. This is a common bone defect model, used to assess regenerative capability of biomaterial scaffolds, stem cells and bone growth factors. Both male and female (50:50) were used for each experimental group as there had not been any report on sex-related difference in healing rate of calvarial defects. A ~2 cm long sagittal incision on the animal head was created. To create the bone defect, a trephine bur was used to remove skull bone and create a full-thickness critical-sized defect (i.e., the smallest defect that would not heal spontaneously) of ~4 mm for mice. Different PLLA scaffolds (piezo or non-piezo layers) with the same sizes were then implanted into the defects.

Signs of pain (e.g., teeth grinding, sitting hunched etc.) were monitored through frequent observations after surgery. All surgical procedures were performed under anesthesia, and euthanasia was performed by standard methods for mice using Commercial Euthanasia Solution.

Experimental design: Table 2 depicts six major animal groups (n=6 animals/group, see statistical analysis below) used for the in vivo experiment. In group #6 (positive control), the bone portion, collected from the process to create the bone defect, was implanted back into the defect to serve as an auto-graft. To minimize cost and resources, the only two endpoints at week 4 and week 8 were performed when the bone grafts were extracted for assessment.

TABLE 2

Designed groups for in vivo study

| Group | Condition | Note |
|---|---|---|
| 1 | non-piezo. PLLA Scaffold | Negative control |
| 2 | ASC + non-piezo. PLLA scaffold + US | Sham |
| 3 | piezo. PLLA scaffold + US | Sham |
| 4 | ASC + piezo. PLLA scaffold | Sham |
| 5 | ASC + piezo. PLLA scaffold + US | Exp. group |
| 6 | Autografts | Positive control |

Selecting ultrasound parameters: For groups #2, #3 and #5, the ultrasound parameters were similar as described above. Yet, to minimize animal number for a limited budget, only two combinations of ultrasound intensity, scaffold design and piezoelectric effect, were selected which had the best osteogenic effects in vitro. If the in vivo outcomes were not positive, other parameters were selected.

The assessments of bone regeneration include (1) mechanical testing, (2) Xray/Micro-CT imaging, and (3) histological analysis, which were based on the ASTM standard guidelines.

Healing is evaluated by mechanical testing with intact bone serving as the benchmark for success. Portions of the implanted bone graft were prepared for compressive, tensile, and torsion loads. Testing was performed on the Instron (MT1-E1) system at a constant axial strain rate and rotation rate to failure. Fracture loads were recorded at the failure point, and modulus or strength of the harvested bone from the stress-strain curve were identified. Torsional properties such as maximum torque, ultimate rotation, torsional rigidity and torsional energy to failure were determined, based on the load-deformation curve. Indentation test to quantify the hardness of extracted bones was also performed.

Bone in-growth within the implants was quantified using cone-beam micro-focus X-ray computed tomography. The 3D images were reconstructed using standard convolution and back-projection algorithms. All of the samples were scanned by micro-CT prior to mechanical and histological analysis. Using cross-sections of the 3D constructs, a global greyscale threshold (newly-formed bones appear darker and scaffolds appear brighter) was employed to detect and quantify the amount of new bone formed, compared to that of the scaffold materials.

At the designated time points an histological analysis was conducted where the harvested tissue samples (n=6) were excised, fixed and stained with Von Kossa (VK) and Toluidine Blue (TB) to evaluate all calcified tissues, and with Goldner's Trichrome to evaluate cellular events. Alkaline Phosphatase (AP) was employed to stain enzymatic activity of bone growth. H&E, and Trichrome Masson (TM) stains were used to identify osteocytes and osteoblasts. Similar to micro-CT, the greyscale threshold algorithm was used to quantify the amount of new bones, relative to the scaffold material.

Through the histological images (H&E, TB, TM etc.), neutrophils, fibrosis, and other inflammation, cells were identified for an assessment of immune-response. Macrophage was specifically stained by using anti-macrophage CD68 antibody, as previously reported. The surrounding tissues were analyzed to search for signs of inflammation and integration between the bone graft and the native tissues.

Figure 7:
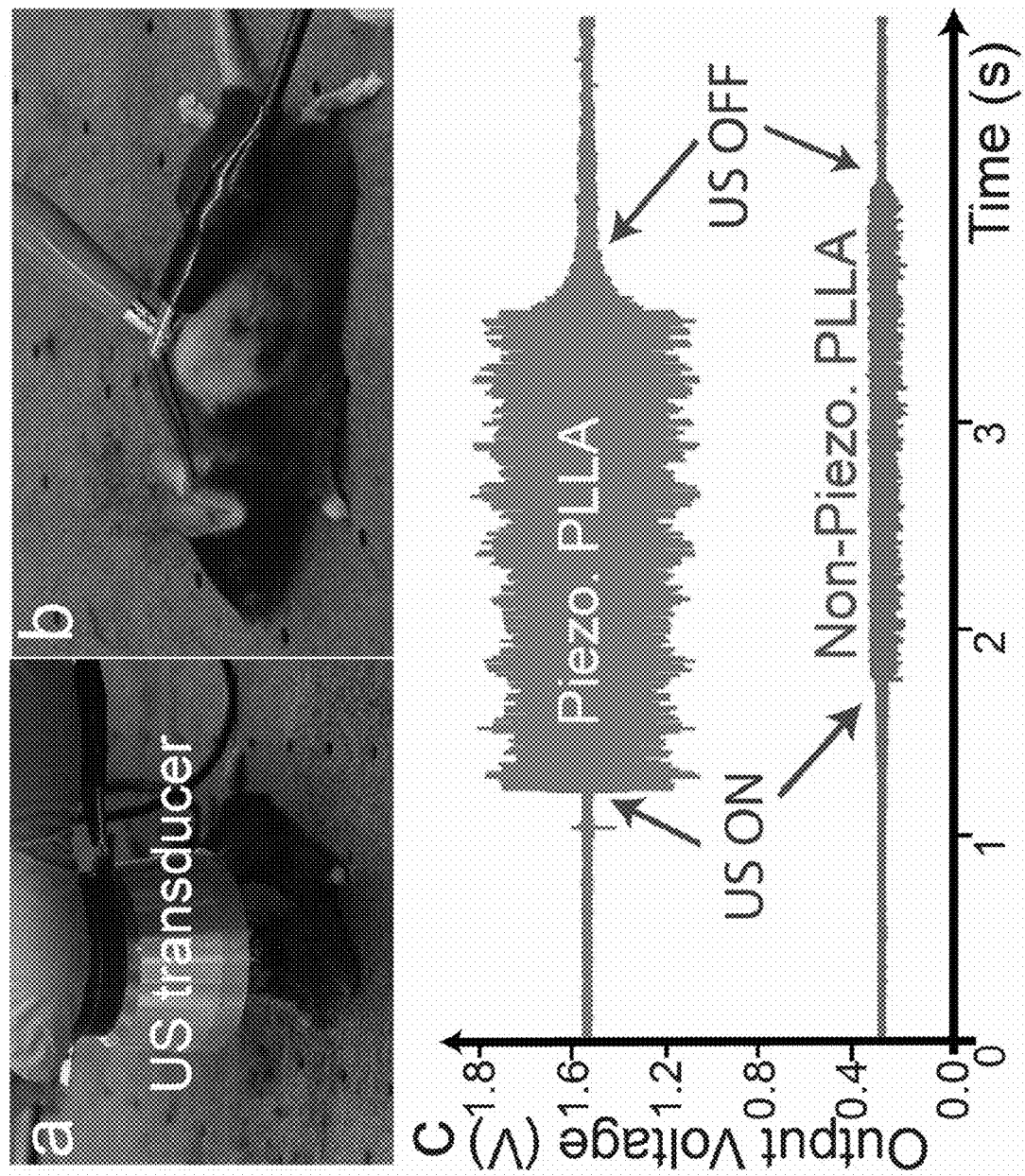
FIG. 7 is testing of ultrasound response from the implanted PLLA scaffold inside calvarial defect of a euthanized mouse. a. Optical image of applying ultrasound on an implanted scaffold. b. Electrodes, coming out from the implanted piezo-PLLA scaffold, were connected to external wires for measuring received ultrasound signals. c. Received signals (charge/voltage) from the implanted piezo-PLLA scaffold, compared to a control, made of non-piezo PLLA scaffold.

Preliminary test: the ultrasound in the designed range (0.2 W/cm² and at 40 kHz) was confirmed to induce a significant electricity on the PLLA piezoelectric scaffold, implanted inside skull/calvarial defects of euthanized mice, while the same ultrasound produced only noise from a non-piezoelectric PLLA sample (FIG. 7).

Figure 8:
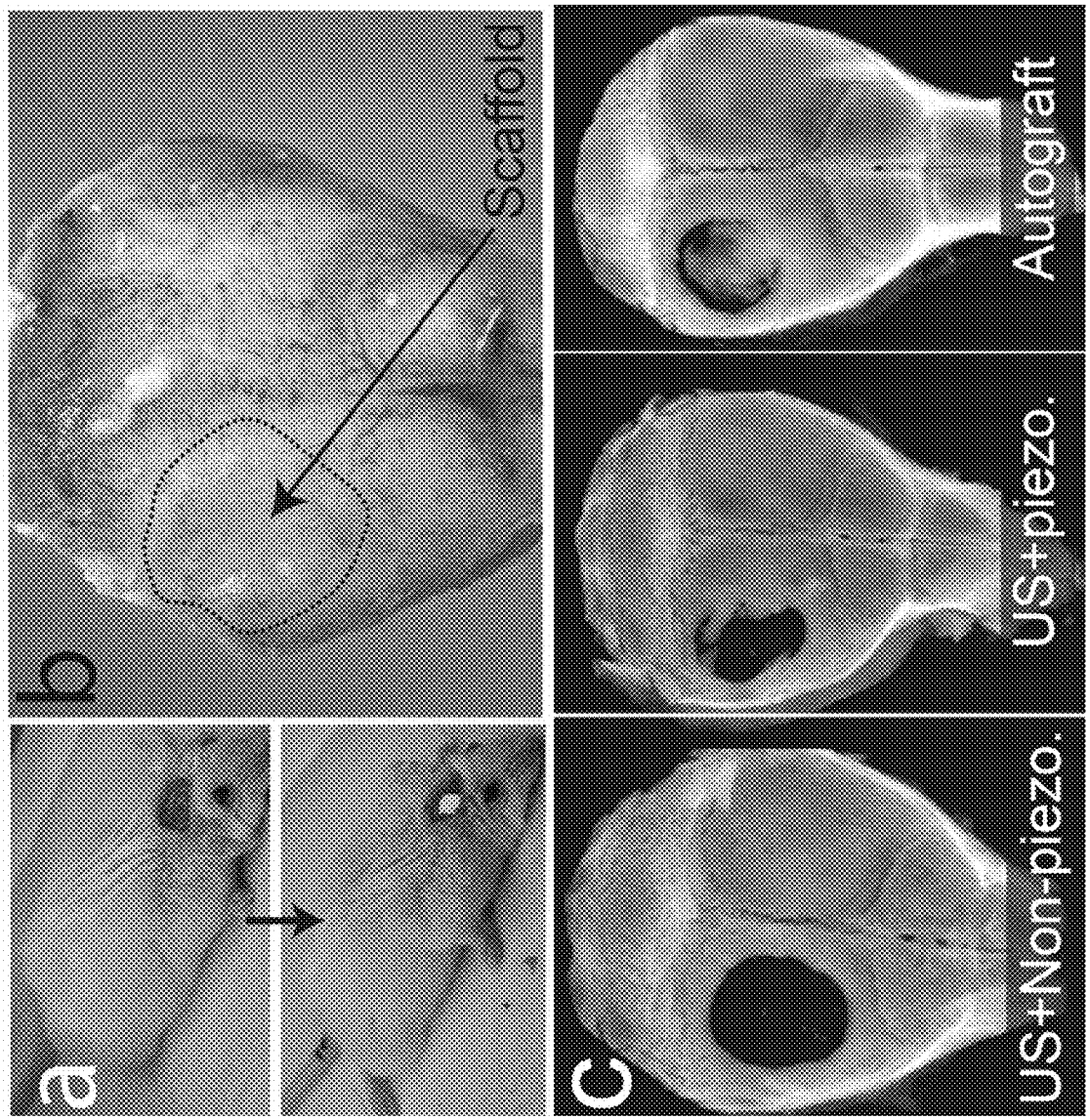
FIG. 8 illustrates implanted PLLA scaffolds without stem cells in skull defects of alive mice. a. Implantation process. b. Extracted calvaria after 3 weeks of implantation. c. X-ray images of extracted skulls after 3 weeks of implantation. Left is a non-piezoelectric scaffold and middle is a piezoelectric scaffold under the same applied ultrasound. Right is the autograft (positive control).

The PLLA nanofiber scaffold (without stem cells) was implanted into skull defects of alive mice (FIG. 8 (at a)) and it was found that the animals well tolerated the scaffolds. As seen in FIG. 8 (at b), the PLLA scaffolds were seamlessly integrated with native skull bone after 3 weeks of implantation. In a pilot study, a piezo-scaffold, a non-piezoelectric scaffold (control) and an autograft were implanted into calvarial defects of mice (n=1 mouse/each) to assess osteoconduction of the scaffold alone, without the stem cells. The scaffolds were subjected to the same ultrasound (as used in FIG. 7) for 14 days. After 21 days of implantation, X-ray images showed that the piezoelectric scaffold exhibited some level of mineralization or bone formation while the non-piezoelectric control had no sign of bone forming under the same applied ultrasound (FIG. 8 (at c)). Also, there was no visible sign of immune-reaction to the implants. It is likely that the piezo-scaffold under ultrasound produced surface charge to promote osteogenic differentiation of host stem-cells, which have migrated into the defect. This implies that; adding ASC cells into the PLLA scaffold, as proposed, would create an ideal solution to significantly enhance bone formation and consequently, heal the bone defect.

It is expected that an enhanced bone formation will be seen in group #5, compared to sham and negative control groups (see table 2) and that the scaffolds in group #5 would exhibit properties (i.e., modulus, stiffness, maximal torque, histological staining etc.) close or equivalent to those of autografts (group #6). Additionally, the scaffolds, which can generate more surface charge, will promote more bone formation. Additionally, a small amount of growth factor, small molecular or some phosphate chemicals etc. could be added which together with surface charge can promote bone regeneration.

Various features and advantages of the invention are set forth in the following claims.

What is claimed is:

1. A method of regenerating bone or tissue, the method comprising:
    applying a scaffold to a wound, the scaffold comprising a plurality of PLLA layers, each layer separated by a hydrogel layer, wherein the PLLA layers comprise a biodegradable nanofiber mesh created by an electrospinning process to exhibit piezoelectricity, wherein the electrospinning process includes rotating a collector drum at a rotation speed between 1,000 and 4,000 RPM, and wherein a piezoelectric constant of the PLLA layers depends at least partially on the rotation speed;
    applying ultrasound energy to the scaffold;
    generating an electrical surface charge on the scaffold; and
    delivering an electrical output to the bone or tissue from the scaffold to regenerate the bone or tissue.

2. The method of claim 1, wherein the ultrasound energy includes an intensity that is less than 0.5 W/cm².

3. The method of claim 1, wherein the ultrasound energy includes a frequency in the kHz range.

4. The method of claim 3, wherein the ultrasound energy includes a frequency at 40 kHz.

5. The method of claim 1, wherein at least one of the PLLA layers includes stem cells.

6. The method of claim 1, wherein at least one of the PLLA layers includes growth factors.

7. The method of claim 6, wherein the growth factors includes BMP-2.

8. The method of claim 1, wherein each PLLA layer includes a thickness of about 25 μm.

9. The method of claim 1, wherein the scaffold includes about 2-10 PLLA layers.

10. The method of claim 1, wherein at least one of the PLLA layers is bonded with a layer of collagen, loaded with calcium phosphate.

11. The method of claim 10, wherein the calcium phosphate is tri-calcium phosphate.

12. A scaffold for regenerating bone or tissue, the scaffold comprising:
    a plurality of PLLA layers comprising a nanofiber mesh, wherein the nanofiber mesh is created by an electrospinning process, and wherein the electrospinning process includes rotating a collector drum at a rotation speed between 1,000 and 4,000 RPM, and wherein the PLLA layers having a piezo constant of 15-20 pC/N resulting at least partially from the rotation speed; and
    a plurality of hydrogel layers, each hydrogel layer positioned between two PLLA layers;
    wherein the plurality of PLLA layers deliver an electric charge to the bone or tissue after ultrasound energy is applied to the plurality of PLLA layers to induce growth of the bone or tissue.

13. The scaffold of claim 12, wherein the plurality of PLLA layers includes 2-10 PLLA layers.

14. The scaffold of claim 12, wherein at least one of the PLLA layers includes stem cells.

15. The scaffold of claim 12, wherein at least one of the PLLA layers includes growth factors.

16. The scaffold of claim 15, wherein the growth factors includes BMP-2.

17. The scaffold of claim 12, wherein each PLLA layer includes a thickness of about 25 μm.

18. The scaffold of claim 12, wherein the nanofiber mesh has a degree of crystallinity of about 70% to about 80%.

19. The scaffold of claim 12, wherein the nanofiber mesh has a crystal alignment of about 0.9 as measured by Herman factor.

* * * * *